US009027383B2

(12) United States Patent
Ritzel et al.

(10) Patent No.: US 9,027,383 B2
(45) Date of Patent: May 12, 2015

(54) SHOCK TUBE APPARATUS FOR BLAST WAVE SIMULATION

(75) Inventors: David V Ritzel, Amherstburg (CA); Steven Parks, Fredericksburg, VA (US)

(73) Assignee: ORA, Inc., Fredericksburg, VA (US)

( * ) Notice: Subject to any disclaimer, the term of this patent is extended or adjusted under 35 U.S.C. 154(b) by 641 days.

(21) Appl. No.: 13/209,545

(22) Filed: Aug. 15, 2011

(65) Prior Publication Data

US 2013/0042665 A1    Feb. 21, 2013

(51) Int. Cl.
*G01N 3/313* (2006.01)
(52) U.S. Cl.
CPC ..................................... *G01N 3/313* (2013.01)
(58) Field of Classification Search
CPC ....................................................... G01N 3/313
USPC ........................... 73/12.01, 12.08, 12.07, 147
See application file for complete search history.

(56) References Cited

U.S. PATENT DOCUMENTS

| 2,824,444 | A | * | 2/1958 | Hanes ........................... 73/12.07 |
| 3,079,786 | A | | 3/1963 | Folwer |
| 3,184,955 | A | | 5/1965 | Filler |
| 3,275,098 | A | * | 9/1966 | Filler ............................ 181/116 |
| 3,326,033 | A | | 6/1967 | Stephenson et al. |
| 3,410,142 | A | | 11/1968 | Daiber et al. |
| 3,495,455 | A | | 2/1970 | Allgood |
| 3,514,071 | A | | 5/1970 | Moffatt |
| 3,578,008 | A | | 5/1971 | Clark |
| 3,711,061 | A | | 1/1973 | Moffatt |
| 3,756,344 | A | | 9/1973 | Daiber et al. |
| 3,873,938 | A | * | 3/1975 | Milling ........................... 372/69 |
| 4,890,603 | A | | 1/1990 | Filler |
| 5,115,665 | A | | 5/1992 | Lacey |
| 5,197,323 | A | * | 3/1993 | Osofsky ........................ 73/12.01 |
| 5,245,868 | A | | 9/1993 | Lacey et al. |
| 5,299,866 | A | | 4/1994 | Osofsky |
| 5,505,081 | A | * | 4/1996 | Lacey et al. ..................... 73/147 |
| 5,542,022 | A | * | 7/1996 | Zauderer ....................... 392/485 |
| 5,606,110 | A | | 2/1997 | Lacey |
| 6,082,635 | A | * | 7/2000 | Seiner et al. ............. 239/265.19 |
| 6,439,891 | B1 | | 8/2002 | Tate |
| 6,763,696 | B1 | * | 7/2004 | Thomas et al. .............. 73/12.09 |
| 2008/0146971 | A1 | * | 6/2008 | Uebelacker et al. .............. 601/4 |
| 2010/0011981 | A1 | | 1/2010 | Carpenter |

OTHER PUBLICATIONS

Hanson Group, Stanford University: Kinetics Shock Tube, Jul. 21, 2010-Aug. 17, 2011.*
Thesis by David A. Russell, Studues of the Effects of Cross-sectional area change and boundary-layer grouth on shock wave motion, 1961.*
K.Y. Zhang and J.J. Gottlieb, Simulation of a Blast Wave in a Shock tube by Using Perforated lates in The Driver, Institute for Aerospace Studies, University of Toronto, Mar. 1986, pp. 1-3, 9, 55, 94.*

(Continued)

*Primary Examiner* — Hezron E Williams
*Assistant Examiner* — Marrit Eyassu
(74) *Attorney, Agent, or Firm* — Law Office of Michael O'Brien

(57) ABSTRACT

This is directed to systems, processes, machines, and other means that simulate blast waves from explosive events. The invention can make waveforms tailored to a user's preference to accurately model a variety of explosive events by utilizing a driver section and a transition section that have divergent geometries.

18 Claims, 9 Drawing Sheets

(56) References Cited

OTHER PUBLICATIONS

D.V. Ritzel, K. Matthews, An adjustable explosion-source model for CFD blast calculations, 21$^{st}$ International Symposium on Shock Waves, Great Keppel Island, Australia, Jul. 20-25, 1997, paper 6500.*

D. Ritzel and K. Matthews, An adjustable explosion-source model for CFD blast calculations. 21st International Symposium on Shock Waves, Great Keppel Island, Australia, Paper 6590 (Jul. 20-25, 1997).

United Facilities Criteria, Structures to resist the effects of accidental explosions. Department of Defence publication UFC 3-340-02 (Dec. 5, 2008).

Charles N. Kingrey, et al., Arrangement for counteracting shock tube rarefaction waves. Statutory Invention Registration H86 (Jul. 2, 1985). See p. 4 col. 3 In. 4 to p. 4 col. In. 12.

* cited by examiner

SHOCK TUBE APPARATUS FOR BLAST WAVE SIMULATION

CROSS REFERENCE TO RELATED APPLICATIONS

Not Applicable

STATEMENT REGARDING FEDERALLY SPONSORED RESEARCH OR DEVELOPMENT

Not Applicable

THE NAMES OF PARTIES TO A JOINT RESEARCH AGREEMENT

Not Applicable

INCORPORATION BY REFERENCE OF MATERIAL SUBMITTED ON A COMPACT DISC

Not Applicable

FIELD OF THE INVENTION

This relates to devices that simulate air blast pressure waves. In some embodiments, the shock waves simulate those generated by an explosive event such as the detonation of a bomb or improvised explosive device (IED), rupture of a pressure vessel or rapid petrol-chemical combustion.

BACKGROUND OF THE INVENTION

Explosive events can be caused by either accidents or deliberate acts. Both of these are extremely dangerous to both people and structures. Engineers study the effect of explosive charges either in field tests or in laboratories. A prerequisite for the experimental investigation of blast effects and injuries, and the consequent development of protective technologies, is the ability to accurately, safely, and reproducibly simulate the air-blast loading conditions caused by an explosion.

Conducting experiments using actual high-explosive charges in field tests is problematic due to cost, availability of qualified sites and personnel, risk of accidents in storage, movement or setting of the charge, rate of testing, quality of extent of data gathering, inherent lack of reproducibility, poor control of the target setup conditions, and the inability to apply advanced instrumentation.

Since the 1800's, the use of laboratory testing has been popular to reproduce gas-dynamic shock waves in a safe and scientific manner. These early devices were versions of the modern gas-dynamic shock tube, which has a variety of uses, from experimental studies of supersonic aerodynamics to combustion. A standard shock tube uses a driver section of a circular cross-section having a constant cross-sectional area with axial distance known as a "conventional geometry." Typically, any inclusions of area expansions in the circular cross-section are highly problematic to fabricate in a matter that would allow gradual and easily defined wall curvature, such that the area change with distance is smooth and gradual.

Scientists and engineers endeavor to use shock tubes to accurately and safely simulate blast conditions in a controlled and repeatable manner to research blast vulnerabilities of systems, detailed processes of blast loading, damages and injuries, as well as to develop countermeasures or protective technologies in a controlled, safe, economic and systematic manner. The shock tubes which accomplish this are called "blast simulators."

A blast wave is a particular type of shock wave characterized by certain profiles or "wave shapes" for pressure, flow velocity, density, and temperature. In a blast simulator a shock wave generated from the "driver section" causes gas to pass through the shock tube to the "test section," where experiments would be conducted, such as studies of blast damage to test articles measured by various devices.

Prior to the disclosed invention, there was a lack of blast simulators which accurately and efficiently replicated blast conditions for scientific investigations. While many have tried, previous blast simulators do not reproduce full and credible blast waveforms leading to the development of protection measures that may be ineffective or in fact deleterious when exposed to actual blast conditions.

BACKGROUND ART

The Hanes U.S. Pat. No. 2,824,444 teaches a device that uses a frangible diaphragm with a shock tube to further drive a moveable piston that is then used to impact a target, producing a mechanical shock for testing. It is not used to generate a blast wave for testing.

The Fowler U.S. Pat. No. 3,079,786 teaches a device that uses a shock tube to accelerate a mechanical mass for impact shock testing of components. It does not teach a driver section and transition section with divergent geometries to generate a true free-field blast wave shape.

The Filler U.S. Pat. No. 3,184,955 teaches a device for amplifying the blast effect from a high explosive charge by using a conical shock tube with the detonating charge at the apex. The device offers no insight on how to simulate the blast waves of high explosives with substances that are not, in fact, the same high explosives.

The Filler U.S. Pat. No. 3,275,098 teaches a conical shock tube used to amplify the shock from the detonation of a small amount of explosive, channelling that shock to the surface of the earth to induce seismic waves for geologic exploration. It does not teach a driver section and transition section with divergent geometries to generate a true free-field blast wave shape.

The Stephenson U.S. Pat. No. 3,326,033 teaches a solution to the problem of reflection in closed shock tubes by putting a screen on the end of an open shock tube. This creates the problem of rarefaction in having an open shock tube, for which no solution is offered. Further, it does not teach a driver section and transition section with divergent geometries to generate a true free-field blast wave shape.

The Daiber U.S. Pat. No. 3,410,142 teaches a conventional geometry blast tube that is driven by high pressure gas generated by heating the driver with concentrically arranged lasers. It does not teach a driver section and transition section with divergent geometries to generate a true free-field blast wave shape.

The Allgood U.S. Pat. No. 3,495,455 teaches a device that is used to produce low-pressure long-duration blast waves to simulate a nuclear blast. It does not teach a driver section and transition section with divergent geometries to generate a true free-field blast wave shape, nor does it explain how the teaching can be applied to short-duration high-pressure blasts.

The Moffatt U.S. Pat. No. 3,514,071 teaches a valve mechanism where the shock wave is produced in the shock tube instead of a frangible membrane. It does not teach a driver section and transition section with divergent geometries to generate a true free-field blast wave shape.

The Clark U.S. Pat. No. 3,578,008 teaches a fast acting plate valve used to actuate a conventional shock tube system only. It does not teach a driver section and transition section with divergent geometries to generate a true free-field blast wave shape.

The Moffatt U.S. Pat. No. 3,711,061 teaches a conventional shock tube actuated by an improved "fluid snap valve" that is more durable than previous valve designs. It does not teach a driver section and transition section with divergent geometries to generate a true free-field blast wave shape.

The Daiber U.S. Pat. No. 3,756,344 teaches a conventional geometry blast tube that is driven by high pressure gas generated by focusing a laser on an orifice at one end of a shock tube. It does not teach a driver section and transition section with divergent geometries to generate a true free-field blast wave shape.

The Kingrey Statutory Invention Registration No. H86 teaches a method for eliminating end-waves by placing several bars placed over the open end of the shock tube and adjusting the spacing between the bars to achieve the rarefaction to reflected ratio. The claimed invention utilizes an end-wave eliminator made of either mesh screen or perforated plates that are adjusted to achieve the same affect. It does not teach a driver section and transition section with divergent geometries to generate a true free-field blast wave shape The Filler U.S. Pat. No. 4,890,603 teaches a device that uses a conical shock tube initiated by a spark to produce a spherically expanding shock wave, which interacts with a diffracting shock wave at the rim of the open end of the shock tube, creating a moving region of high pressure within the human body that then locally fractures kidney stones. It does not use of a driver section and transition section with divergent geometries to generate a true free-field blast wave shape.

The Lacey U.S. Pat. No. 5,115,665 teaches a free-piston shock tube that uses a piston to compress the driver gas and then rupture the driver membrane for use in situations where the user desires very high pressure and high temperature shocks of a long duration for aerodynamic studies. FIG. 1C shows a conical expansion between the driver and test sections, but the description does not teach the meaning of this construction. Rather it indicates this feature is unnecessary in its preferred embodiment. It does not teach a driver section and transition section with divergent geometries to generate a true free-field blast wave shape.

The Lacey, et al. U.S. Pat. No. 5,245,868 teaches the operation of a stop mechanism for the compression piston in a free-piston shock tube similar to Lacey U.S. Pat. No. 5,115,665 above. Again, it does not teach a driver section and transition section with divergent geometries to generate a true free-field blast wave shape.

The Osofsky U.S. Pat. No. 5,299,866 teaches the use of a pebble bed heater to heat the driver gas in a conventional shock tube to improve performance when simulating a nuclear blast. The device uses an expansion section to connect a smaller driver section to a larger test section, but does not teach how this affects waveforms. It does not teach a driver section and transition section with divergent geometries to generate a true free-field blast wave shape.

The Lacey U.S. Pat. No. 5,505,081 teaches a valve assembly to actuate the free piston shock tube tunnel in Lacey U.S. Pat. No. 5,115,665 above. The patent does not teach anything about the generation of true free-field blast waves.

The Lacey U.S. Pat. No. 5,606,110 teaches a diaphragm design for the shock tube of Lacey U.S. Pat. No. 5,115,665 above, with multiple rupture areas. It does not teach a driver section and transition section with divergent geometries to generate a true free-field blast wave shape.

The Ritzel et al. paper, An adjustable explosion-source model for CFD [computational fluid dynamic] blast calculations raises the prospect that a more accurate method of modeling explosions can exist by using helium balloons to simulate explosions. It does not teach how to make a blast wave simulator to model these explosions.

The Tate U.S. Pat. No. 6,439,891 teaches a shock tube that uses a high speed valve in place of a rupture membrane. The patent is concerned with the design of the high speed valve and does not claim to use divergent driver or transition section geometry to generate true free-field blast waves.

The Thomas, et al. U.S. Pat. No. 6,763,696 teaches a shock tube system composed of a cylindrical driver, an extension section to extend the driver length, an expansion section, and a test section with a larger cross section than driver or extension section. The patent does not teach anything about divergent driver geometry or that the expansion section referenced is anything other than a convenient way to go from the smaller-area driver/extension section to the larger-area test section. The patent also does not teach that the divergent geometry of the expansion section is required for the wave shape tailoring the inventors claim.

The Unified Facilities Criteria publication *Structures to resist the effects of accidental explosions* provides a model for simulating only the first phase of a free-field explosion. It does not teach a how to make a blast wave simulator to model these explosions.

The Carpenter U.S. Pat. App. Pub. No. 2010/0011981A1 teaches a device that generates a shock wave using a tube and a fast acting valve to generate noise signatures for IED training. It does not teach a driver section and transition section with divergent geometries to generate a true free-field blast wave shape.

BRIEF SUMMARY OF THE INVENTION

Methods, systems, and other means are provided for explosive blast testing. In accordance with some embodiments, a machine simulates the transient air shock-wave conditions generated by an explosive event. This machine can be a specially shaped and designed gas-dynamic shock tube. The disclosed invention is a blast simulator comprising four continuous sections: a first section called a "driver section," a second section called a "transition section," a third section called a "test section," and a fourth section called an "end-wave eliminator."

The driver section comprises a special shaped duct with two ends. The first end is closed and converges into an apex. From the apex, the duct has a diverging area which leads to a second end that contains a frangible membrane. The driver section receives an input of compressed gas, which pressurizes the driver section until the frangible membrane ruptures from over-pressurization, or is mechanically ruptured by a cutting device.

After passing through the first frangible membrane, the compressed gas enters the transition section. The transition section smoothly channels the expanding gas and propagated wave from the driver section into a second "test section." In this regard, the transition section performs two functions. First, it must allow for the initial expansion of gasses at the same rate developed from the driver section for some distance such that the required shock waveform is properly developed. Second, once that shock waveform is developed, the shock-wave flow must be smoothly redirected or converged into the test section where users can conduct experiments. If the flow is not re-converged, the shock-wave amplitude will decay too rapidly. The transition section may contain louvered apertures in the side wall to adjust waveforms as necessary, depending on the test involved.

The test section is typically used for the placement of a test object, or target, and contains test objects, structures or materials that react to the shock waveforms, creating results germane to the desired outputs of a user. However, experiments can be conducted close to the first frangible membrane in the transition section, if especially high loading levels are desired. Those tests simulate explosive events such as bombs, IEDs, and petro-chemical explosions. One difficulty in obtaining accurate results is the Law of Reflection, which states that waveforms reflect off objects in their surroundings and return to the wave source. The present invention eliminates that concern by use of the end-wave eliminator.

After the waveform leaves the test section, it enters the end-wave eliminator. The end-wave eliminator is located at the end of the test section and comprises a shock-diffuser element within an enclosing dump tank having an anechoic liner at the end of the test section. The end-wave eliminator serves two functions. First, it prevents a wave which has passed through the test section from being reflected back into the test section, harming the experimental results. Second, the end-wave eliminator possesses sufficient volume to contain the efflux of gas from the test section and, with its anechoic lines, serves to muffle the pressure disturbance which would otherwise be propagated into the external laboratory workspace.

BRIEF DESCRIPTION OF THE SEVERAL VIEWS OF THE DRAWINGS

Figure 1:
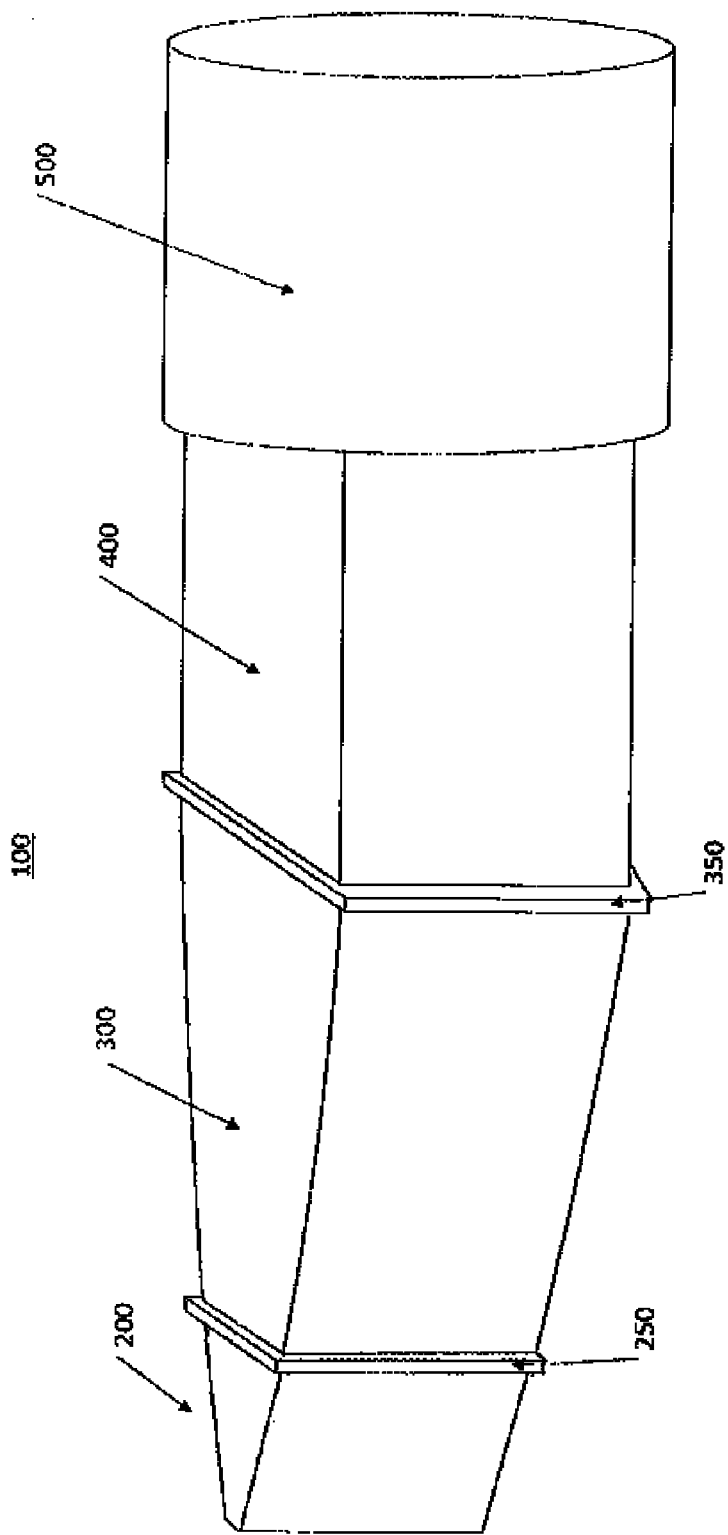

Having thus described the invention in general terms, reference will now be made to the accompanying drawings, which are not necessarily drawn to scale, and wherein:

FIG. 1 is an explanatory illustration of a blast wave simulator in accordance with some embodiments of the present invention.

Figure 2:
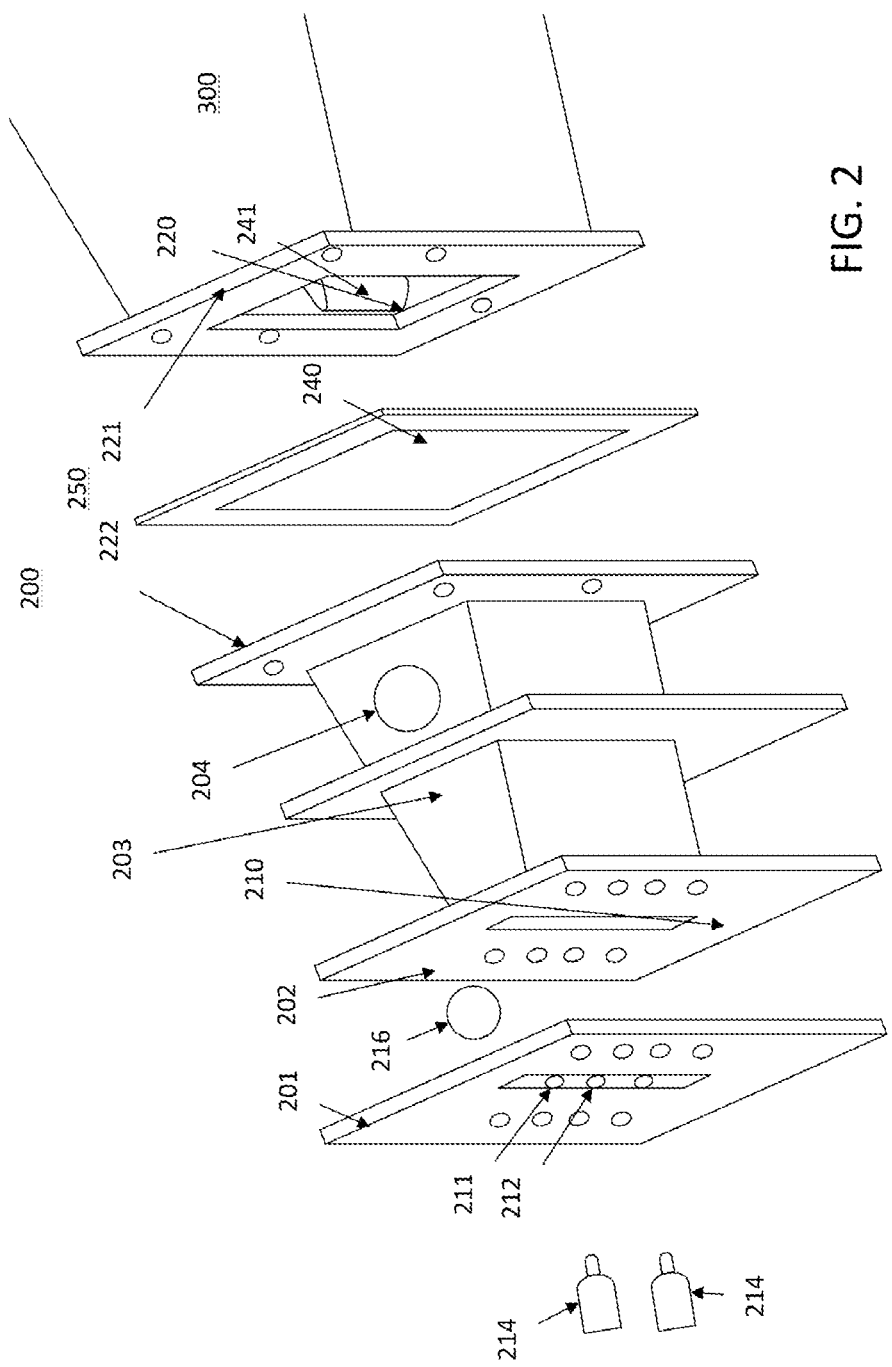

FIG. 2 is an explanatory illustration of the driver section of a blast wave simulator in accordance with some embodiments of the present invention.

Figure 3A:
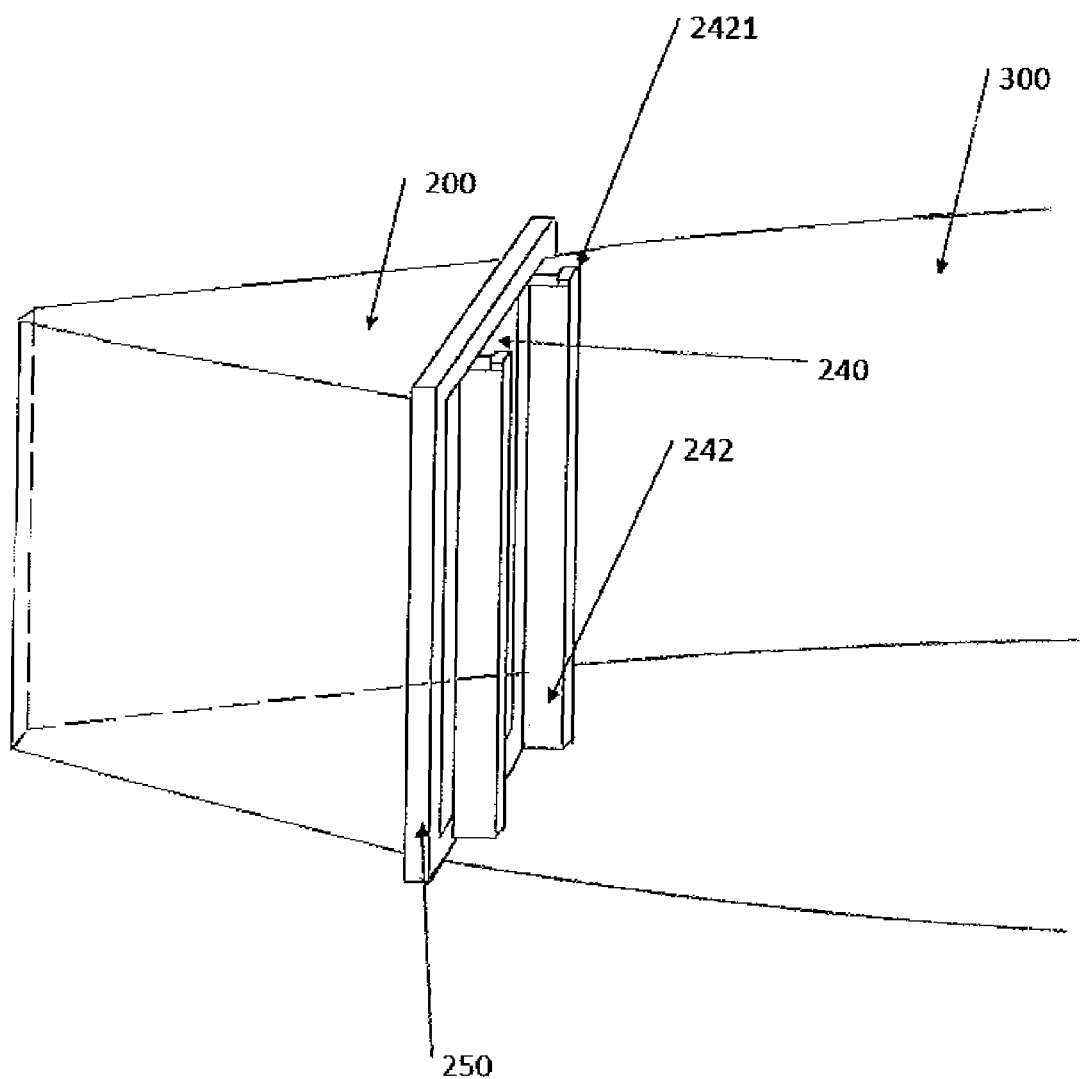
Figure 3B:
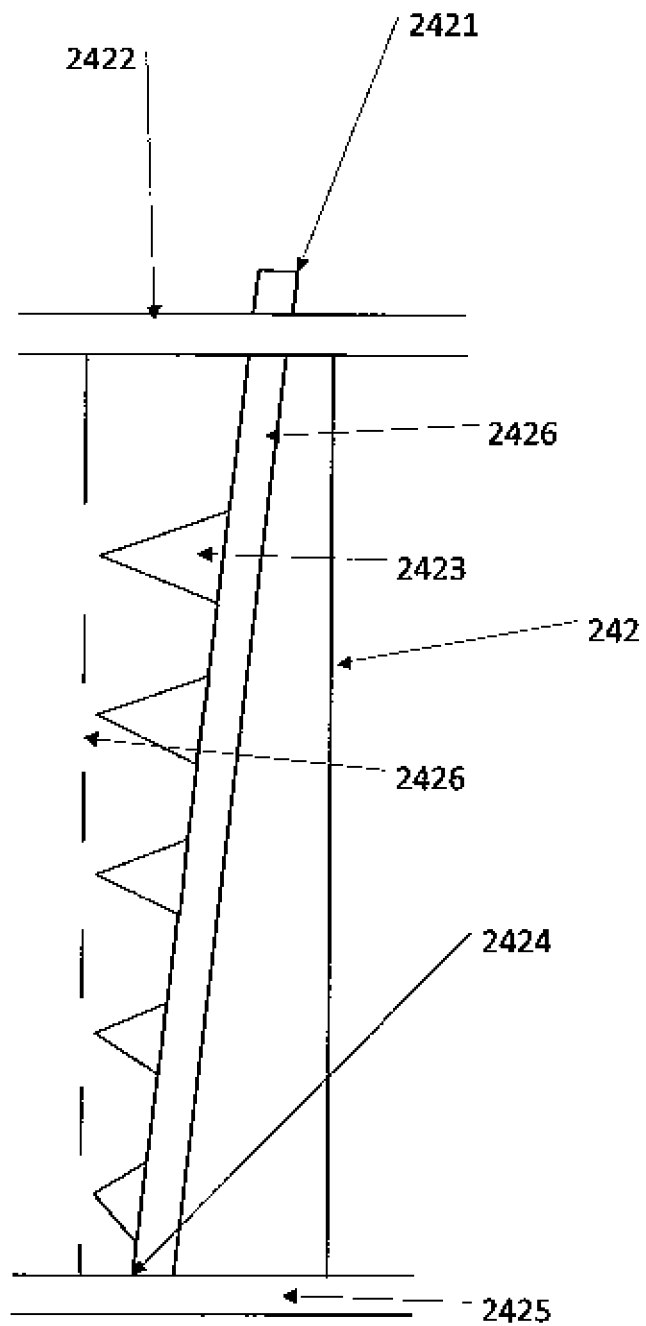

FIGS. 3A and 3B are explanatory illustration of a device to cut the frangible membrane of a blast wave simulator in accordance with some embodiments of the present invention.

Figure 4:
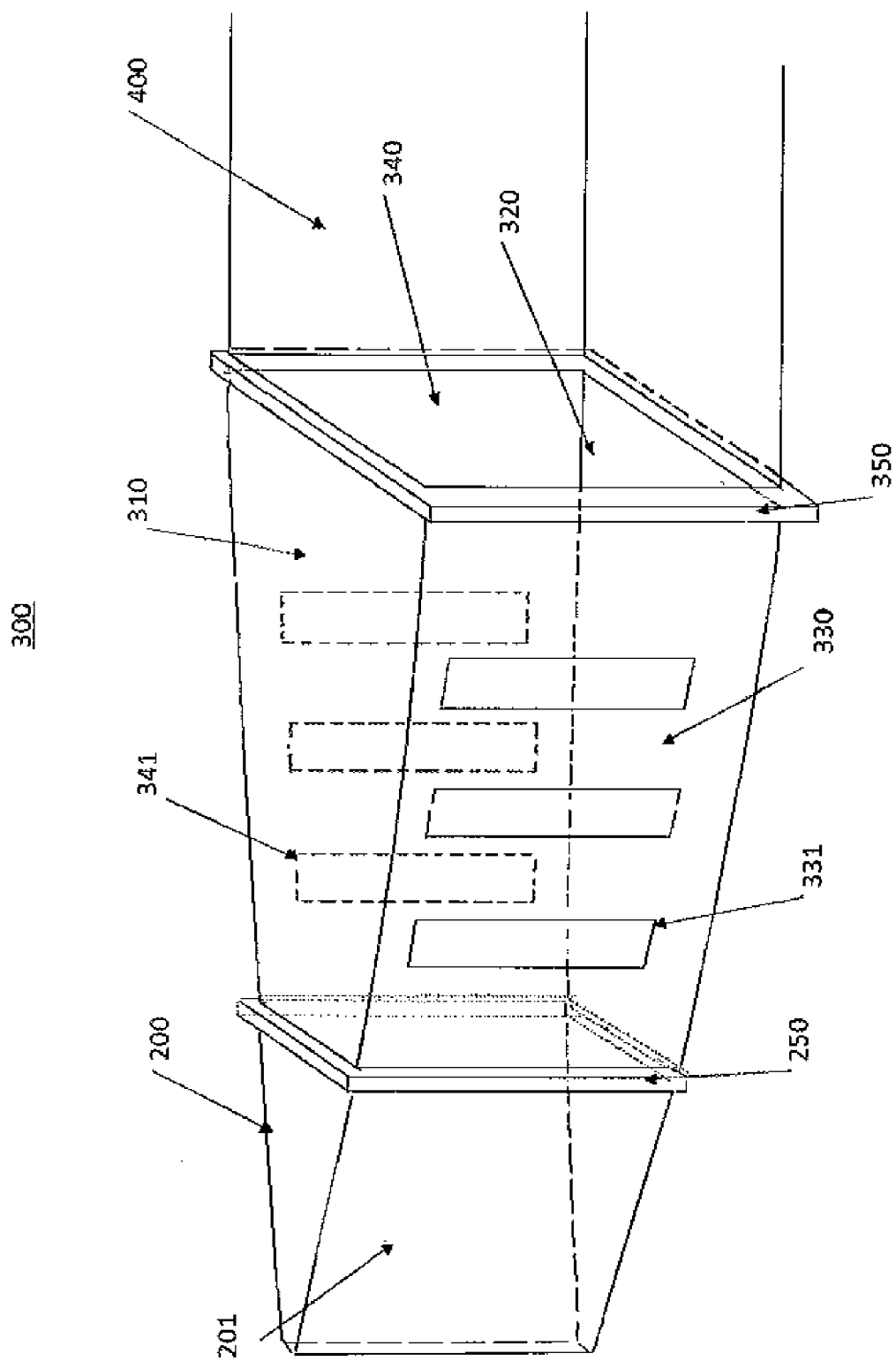

FIG. 4 is an explanatory illustration of the transition section of a blast wave simulator in accordance with some embodiments of the present invention.

Figure 5:
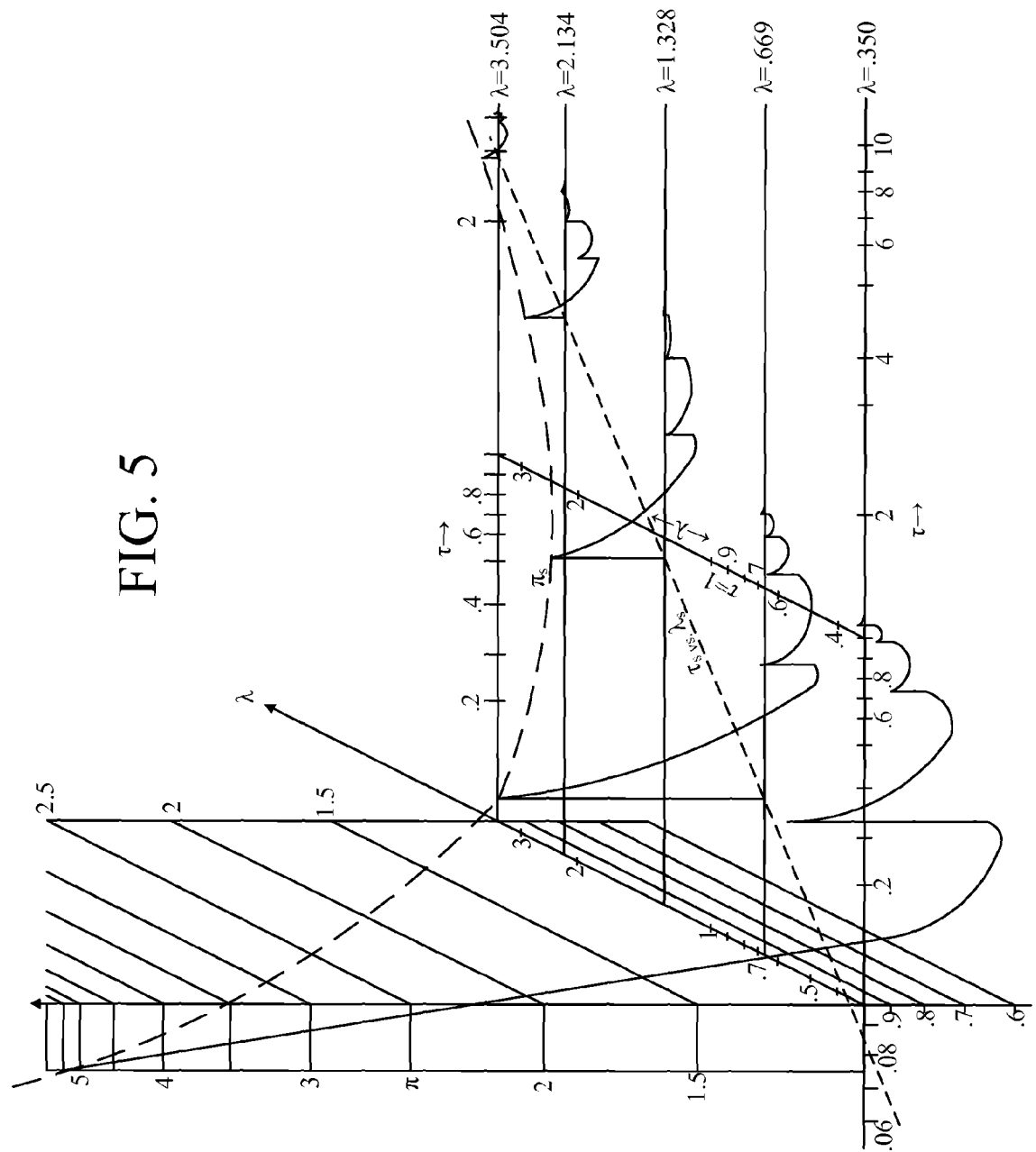

FIG. 5 is a graph of a model blast wave behavior over pressure, time and distance.

FIG. 6A-D is a series of descriptions of different drivers.

Figure 7:
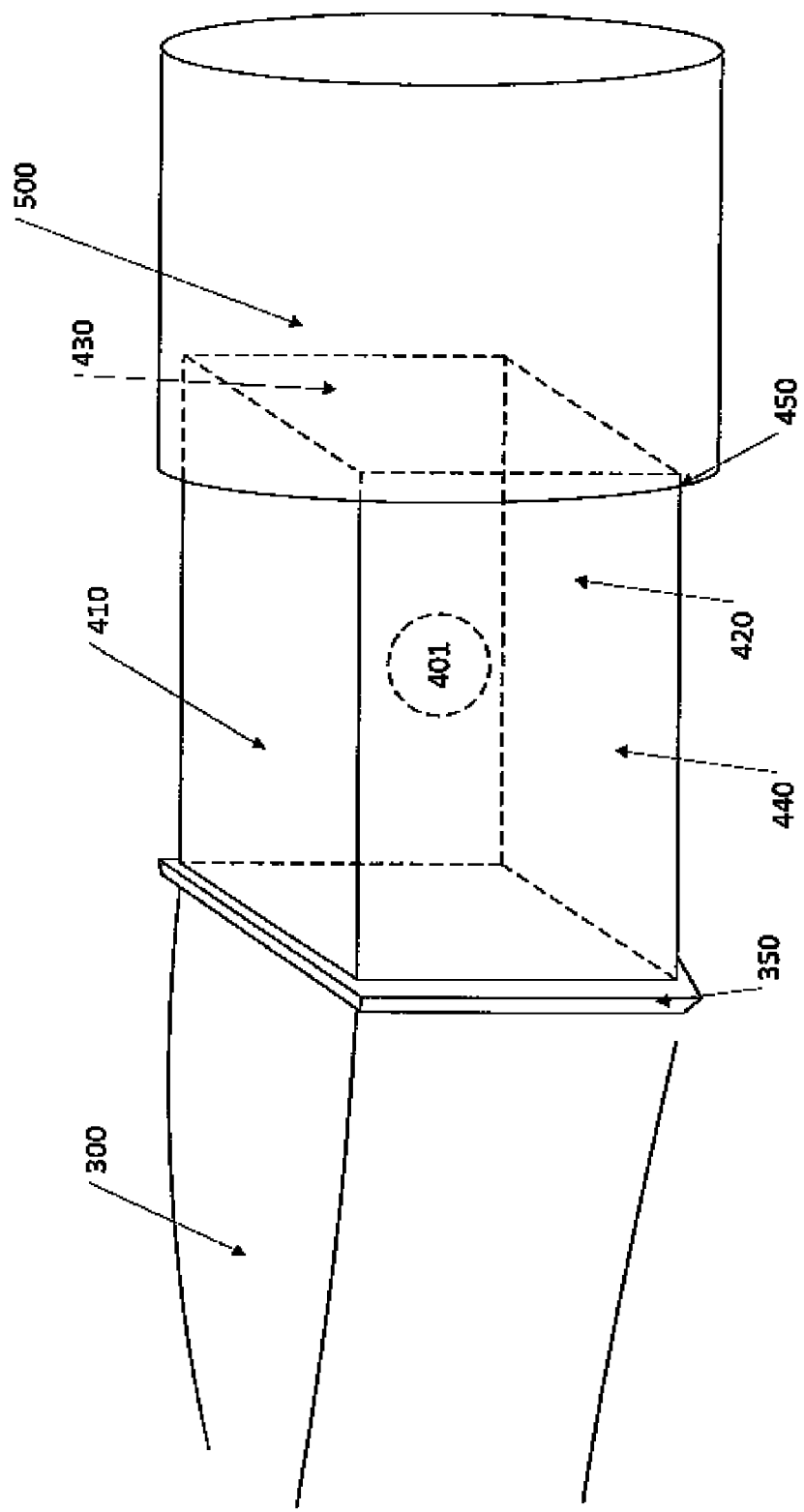

FIG. 7 is an explanatory illustration of the test section of a blast wave simulator in accordance with some embodiments of the present invention.

Figure 8:
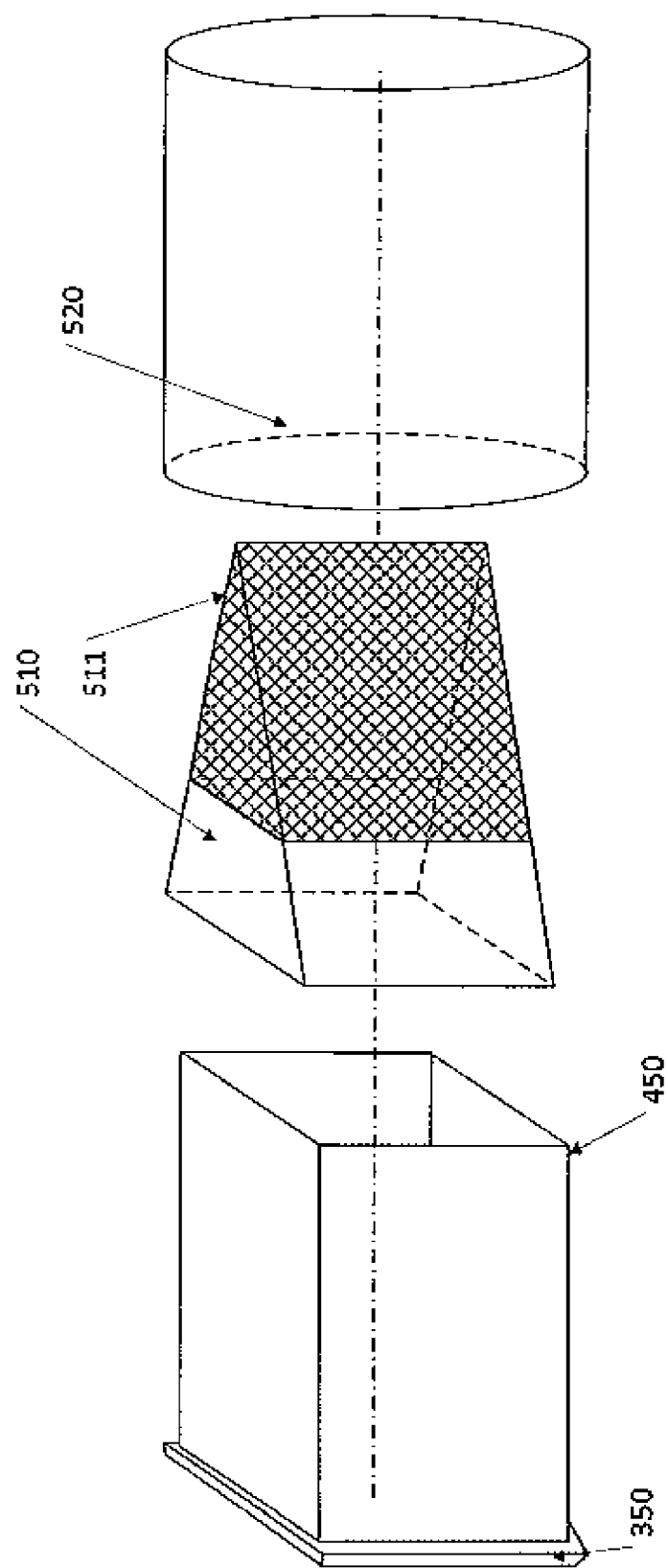

FIG. 8 is an explanatory illustration of the end-wave eliminator of a blast wave simulator in accordance with some embodiments of the present invention.

DETAILED DESCRIPTION OF THE INVENTION

Shock tubes were built to simulate air blast pressure waves from nuclear explosions since the Atmospheric Nuclear Test Ban Treaty of 1963 prohibited live-fire testing. The shock tubes generally performed well, simulating an air blast that lasted for 1000 ms at 1 MPa. These shock tubes were a straight piece of pipe open at one end and separated into a "driver" section with a high pressure gas and a "driven" section with a low-pressure test target and open to ambient conditions. The two sections would be separated by a frangible membrane. The driver would be pressurized until the frangible membrane either ruptured from over-pressurization or by a puncturing device.

There are two basic problems with this design. First, it did not accurately replicate air blast waves from nuclear explosions. Second, it did not accurately replicate air blast waves from hemispherical high energy blast sources.

There are four basic problems with the traditional blast-tube's simulation of the air blast resulting from a nuclear explosion. First, unless the driver gas is specially heated, its cooling upon expansion will cause a density and temperature discontinuity to develop when interfacing with the air it is pressurizing, resulting in anomalous waveforms. Second, an open-ended shock tube will result in a greatly exaggerated outflow and the development of a recompression shock traveling upstream, that is, contrary to a true explosive blast. Third, an inefficient frangible membrane rupture will result in remnants of the frangible membrane obstructing the pressurized air leaving the driver. Fourth, an explosion in an enclosed space such as a laboratory is extremely loud and disruptive to anyone else trying to do work, even in a large facility.

There are three additional problems with using techniques appropriate to modern air-blast wave concerns. First, there are different types of explosive threats, including high explosives, fuel-air explosions, non-conventional heterogeneous formulations, and non-spherical charges, which tend to have higher peak over-pressure conditions, because the impulse is around 10 ms, or 1% of the length of time-scale of an air blast from a nuclear detonation. Second, these different kinds of explosive incidents have secondary shocks. Many non-conventional structures and humans are sensitive to the negative phase of a high explosive blast, which cannot be simulated in the traditional shock tube. When a high explosive detonation occurs, for example, there is a shock compression followed by an abrupt expansion. Both of these are relevant to human injury—particularly brain injury—but the traditional shock tube can only accurately simulate the former. Third, non-nuclear explosive events create waveforms that have higher amplitude, shorter duration, and some manner of negative phase, including the secondary shock.

Embodiments of the present invention overcome many of the obstacles associated with producing waveforms that simulate explosive events, and now will be described more fully hereinafter with reference to the accompanying drawings that show some, but not all embodiments of the claimed inventions. Indeed, the invention may be embodied in many different forms and should not be construed as limited to the embodiments set forth herein. Rather, these embodiments are provided so that this disclosure will satisfy applicable legal requirements. Like numbers refer to like elements throughout.

FIG. 1 shows blast simulator 100. Blast simulator 100 is a duct. Blast simulator 100 can be used to, among other things, create waveforms that replicate the waveforms created by IEDs, bomb blasts, and petro-chemical explosions. Once those waveforms are created, they can be used to test impact on material within blast simulator 100.

Blast simulator 100 includes driver section 200. Driver section 200 is coupled to transition section 300 with contains a mechanical couple 250. Transition section 300 is coupled to test section 400 with mechanical couple 350. Test section 400 is coupled to end-wave eliminator 500 with a mechanical couple (not shown).

In one embodiment, blast simulator 100 functions when an explosive event occurs in driver section 200 (see FIG. 2). The explosive charge creates a waveform that passes through mechanical couple 250 (see FIGS. 2, 3) and enters transition section 300 (see FIG. 4). From transition section 300, the waveform passes through mechanical couple 350 (see FIG. 4) and enters test section 400 where it may react with a target (see FIG. 5). The waveform which does not have exposure to the target then enters end-wave eliminator 500, where it is dissipated.

FIG. 2 shows driver section 200. Driver section 200 contains a first end 210 that is especially shaped and has an area divergent from a second end, which contains apex 220. Apex 220 has a mechanical couple 250 to frangible membrane 240. In one embodiment, driver section 200 contains a removable back plate 201. In a first operating mode, removable back plate 201 contains port 211, which allows for the input of a combustible gaseous mixture, such as oxy-acetylene. Removable back plate 201 contains port 212, which allows for the insertion of a firing plug to ignite the compressed gas inserted through port 211. In some embodiments, multiple ports can provide for a set of firing plugs 214. In that embodiment a set of firing plugs 214 ignite the compressed gas inserted through port 211. Removable back plate 201 can be attached to flange 202 with bolts. In a second operating mode, removable back plate 201 can have port 211 blocked and port 212 can be used to insert inert compressed gas to pressurize driving section 200. In a third operating mode, a balloon 216 made of made of tough reinforced fabric such as vinyl or sheet plastic such as polyethylene can be inserted into driver section 200 and inflated with an inert gas. The rupture of the balloon 216 either by over-pressurization or by a cutting device such as cutting mechanism 242 to create a pressure wave. Reinforcement rib 203 is not required, but can provide additional stability for driver section 200. Air-eductor purge port 204 can be blanked for compressed gas mode or used to provide air to allow flammable gas to ignite in flammable gas mode. Apex 220 contains flange 221, which has a mechanical couple 250 to flange 222 with an o-ring (not pictured), as necessary. Frangible membrane 240 is reinforced by cutting mechanism 242. Frangible membrane 240 can also be punctured by cutting mechanism 242. Frangible membrane 240 is unnecessary in the third operating mode because a balloon 216 serves as the frangible membrane as explained below.

The purpose of driver section 200 is to create a pressure wave for blast simulator 100. There are three ways of accomplishing this which use three different sets of equipment in each case the equipment pressurizes the driver section combines with an even which causes the frangible membrane to rupture creating a pressure wave. In the first operating mode, needed equipment can include a device that inserts flammable gas into driver section 200 through port 211 which becomes a flammable gas inlet. That gas is then ignited by a firing plug 214 inserted into port 212 creating an ignited gas mixture. The ignited gas mixture pressurizes driver section 200. The ignited gas mixture creates a pressure wave when it travels through mechanical couple 250 upon the rupture of frangible membrane 240. Frangible membrane 240 can be ruptured either by over-pressurization or by cutting mechanism 242, which is explained in more detail below. The ignited gas mixture expands from driver section 200 into transition section 300, creating a pressure wave.

In the second operating mode, needed equipment can include a pumping device that fills driver section 200 with compressed gas though port 211. The pumping device could be, for example, an air compressor. Air-eductor purge port 204 is covered in the second operating mode. The compressed gas creates a pressure wave when it travels through mechanical couple 250 upon the rupture of frangible membrane 240. Frangible membrane 240 can be ruptured either by over-pressurization or by cutting mechanism 242 which is explained in more detail below.

In the third operating mode, the requires equipment that includes a balloon 216 inserted into driver section 200 and an inflation device attached to port 211 to pressurize the balloon 216. The inflation device could be, for example, an air compressor. Air-eductor purge port 204 and port 212 are blocked in the third operating mode. Frangible membrane 240 is removed and the frangible membrane becomes the balloon 216 itself. Cutting mechanism 242 is mounted in transition section 300 (see FIG. 3A, 3B). The inflation device pressurizes the balloon 216 to a desired level, at which point the balloon 216 can be ruptured by cutting mechanism 242 creating a pressure wave. The third operating mode, can be used, for example, in large scale operations.

FIG. 3A shows the location of cutting mechanism 242. Cutting mechanism 242 is located within transition section 300 and just downstream of mechanical couple 250. In some embodiments, cutting mechanism 242 has the shape of an aerodynamic wing that is immediately adjacent to frangible membrane 240. Until a set of cutting teeth (not pictured) are activated with switch 2421, cutting mechanism 242 acts as a support strut for frangible membrane 240. Cutting mechanism 242 can be a single support strut, or a plurality of support struts, depending on the needs of the user. However, the construction and use technique of cutting mechanism 242 is similar in all three operating modes.

FIG. 3B shows a cross-sectional view of cutting mechanism 242. Cutting mechanism 242 can be mounted into transition section 300 with top mounting bracket 2422 and bottom mounting bracket 2425. Inside of cutting mechanism 242 is a set of cutting teeth 2423. Cutting teeth 2423 are of non-uniform size and mounted onto bracket 2426. Bracket 2426 pivots on pivot point 2424. When switch 2421 is activated, bracket 2426 pivots about pivot point 2424, causing cutting teeth 2423 to pass through slots 2426, and then rupture a frangible membrane (not pictured).

As noted above, one of the problems with previous shock tubes is the inability to rupture a frangible membrane without having the remnants of the frangible membrane obstructing the flow of the compressed gas leaving the driver section. The present invention resolves this problem with a unique cutting mechanism to rupture the diaphragm without forming anomalous waves. The present invention does this by combining an aerodynamic wing with a series of holes that can deploy a plurality of teeth that efficiently sever the frangible membrane.

Cutting mechanism 242 can be constructed with a number of machining techniques. For example, a 3/16 inch sheet of 1040 steel can be bent to form the shape of cutting mechanism 242. The ends of the sheet can then be welded together, and a metal cutting device can then be used to cut a series of slots 2426 in cutting mechanism 242. Cutting teeth 2423 can be attached to bracket 2426 by welding, or both components can be manufactured as one piece of metal. Pivot point 2424 can be as simple as a bolt through bracket 2426, or can be more elaborate depending on the embodiment utilized. The machinist can then insert bracket 2426 into cutting mechanism 242, attach pivot point 2424, and then utilize switch 2421 to activate cutting mechanism 242.

As noted above, one of the problems with previous shock tubes has to do with the Second Law of Thermodynamics. When compressed gas passes from the driver, it expands, loses energy, creates entropy and, as a result, malforms the compression wave. Previous shock tubes resolved the problem of waveform energy dissipation by heating the compressed gas, which adds energy to the compressed gas. However, these solutions are limited in their effectiveness because the form of the pressure wave is equally important as the energy in it. The present invention takes a new approach by using the transition section to adjust the waveform to resemble model waves as depicted in scientific journals.

FIG. 4 shows transition section 300. In one embodiment, transition section 300 contains a first wall 310, a second wall 320, a third wall 330, and a fourth wall 340. First wall 310 is parallel to second wall 320. The shape of third wall 330 and fourth wall 340 are defined by a mathematical shape function. The mathematical shape function has a first derivative which defines the slope of the wall. Third wall 330 and fourth wall 340 are "smooth" when the first derivative of the mathematical shape function is continuous from mechanical couple 250 to mechanical couple 350, and when the second derivative of the mechanical shape function is low order and continuous. In one embodiment, third wall 330 and fourth wall 340 are smooth. Third wall 330 and fourth wall 340 are collectively known as a set of side walls.

It is well known that curves can be fitted with polynomials of different orders. Higher order polynomials have more inflection points and therefore are more likely to fit more points on a curve. However, this patent teaches that the equation which models each sidewall must be continuous in the first and second derivative and use low order polynomials in the second order. The smooth curves caused by these functions prevent anomalous waves.

One embodiment may require the testing of material that blocks the cross-sectional area of test section 300. Such material is subject to reflected shockwave conditions because the shockwave will reflect back to the closed end of driver 200, which may be back plate 201 in some embodiments. To mitigate that problem, louvered apertures 331 and 341 may be inserted into sidewalls 330 and 340 respectively to allow reflected shock waves from the encounter to vent externally from the blast wave simulator. Louvered apertures 331 and 341 can be rapidly opened by various mechanical methods after passage of the initial downstream shockwave. Alternatively, in some embodiments, the pressure from the initial shockwave can open louvered apertures 331 and 341.

FIG. 5 shows a graph of Dr. Harold Brode's well-known classical solution for a pressure wave at a specified time and distance from a spherical explosion of trinitrotoluene (TNT). The axes are labeled in the same manner as in Dr. Brode's paper. The $\tau$-axis represents time from the explosive event, with the origin being the incident of the explosive event. The $\pi$-axis measures pressure, with the origin being atmospheric pressure. The $\lambda$-axis represents distance from the explosive event, with the origin being the epicenter. The explosive event initially causes a primary shock phase where the pressure is initially high, then the wave enters a first phase of compression below atmospheric pressure, then a secondary shock phase creates a second impulse, followed by a second phase of compression.

As noted above, one of the difficulties facing previous shock tube configurations was the ability to recreate this pattern of primary shock and secondary shock, particularly with the short impulse times of non-nuclear explosions. Previous inventions dealt with this issue by heating the compressed gas at the transition section inlet. As explained in FIGS. 6A-6D, the present invention resolves that problem by adjusting the physical geometry of the driver section, or first part, and transition section, or second part, which is collectively a shock tube driver known as the "wedge." The physical geometry enables the wedge to control the waveform.

In each of the drawings 6A-6D the driver section has a physical geometry divergent from the transition section. In each drawing that divergent physical geometry has an effect on the waveform that leaves the transition section as shown in the two graphs.

Figure 6A:
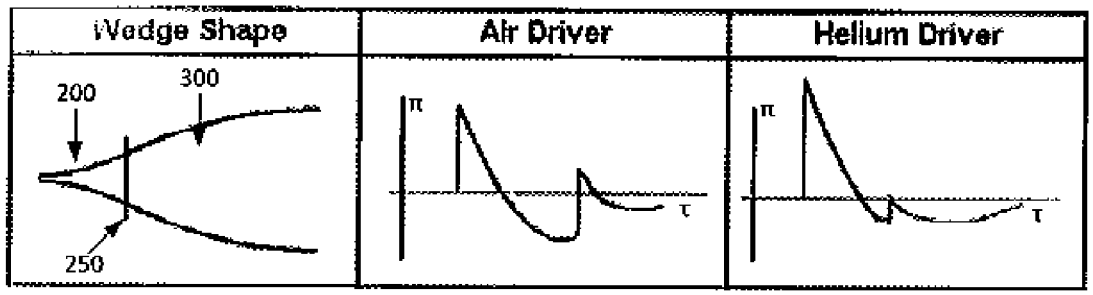

FIG. 6A shows a wedge having a physical geometry defined where driver section 200 contains a positive curvature, and transition section 300 contains an inflected curvature separated by mechanical couple 250. The adjacent graphs show the pressure-time relationship of this wedge configuration modeling a TNT detonation when the compressed gas is either air or helium, in a large test section with a short duration explosive event.

Figure 6B:
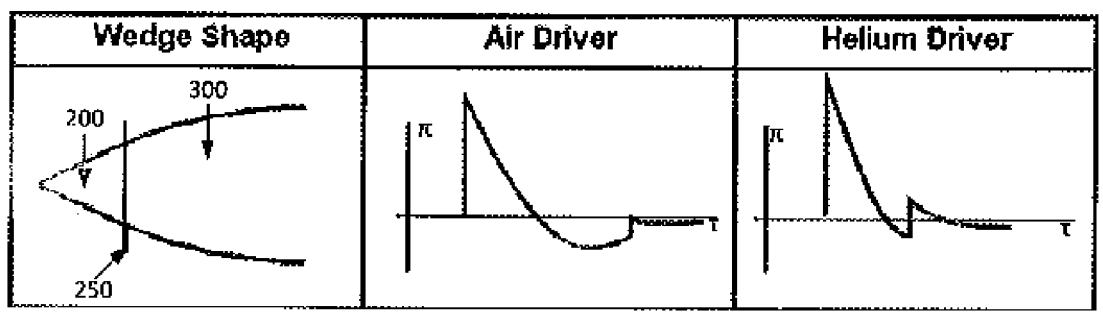

FIG. 6B shows a wedge having a physical geometry defined where driver section 200 contains a linear curvature, and transition section 300 contains a convergent curvature separated by mechanical couple 250. The adjacent graphs show the pressure-time relationship of this wedge configuration modeling a TNT detonation when the compressed gas is either air or helium, in a large test section with a short duration explosive event.

Figure 6C:
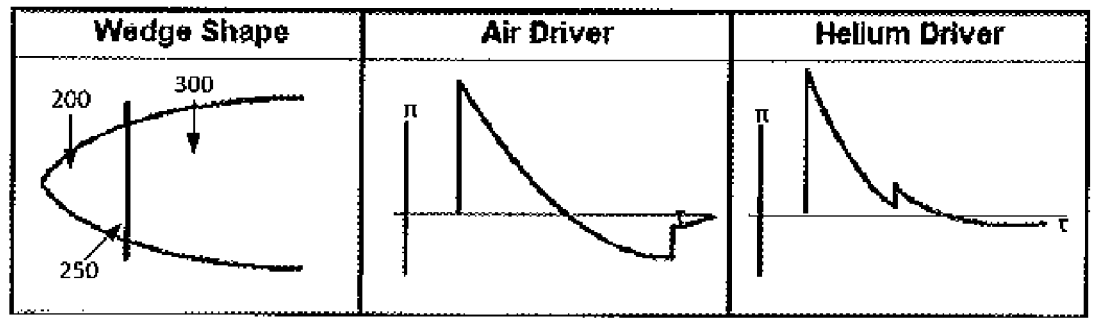

FIG. 6C shows a wedge having a physical geometry defined where driver section 200 contains a negative curvature, and transition section 300 contains a convergent curvature separated by mechanical couple 250. The adjacent graphs show the pressure-time relationship of this wedge configuration modeling a TNT detonation when the compressed gas is either air or helium, in a large test section with a short duration explosive event.

Figure 6D:
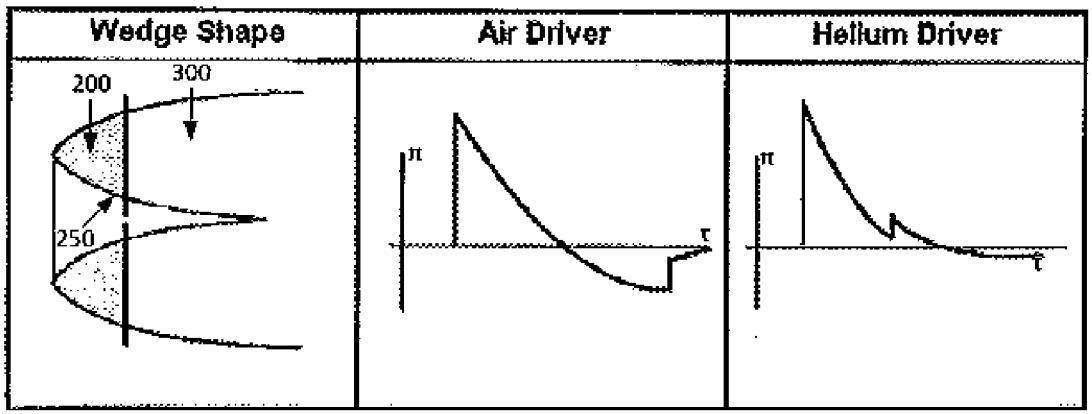

FIG. 6D shows a wedge having a physical geometry defined where driver section 200 is a plurality of shock tube drivers containing a positive curvature and transition section 300 contains an inflected curvature separated by mechanical couple 250. The adjacent graphs show the pressure-time relationship of this wedge configuration modeling a TNT detonation when the compressed gas is either air or helium, in a large test section with a short duration explosive event.

FIG. 7 shows test section 400. Test section 400 is a duct that has a mechanical couple 350 to transition section 300. Test section 400 has a mechanical couple 450 to end-wave eliminator 500. Test section 400 has four walls: first wall 410, second wall 420, third wall 430, and fourth wall 440. First wall 410 is parallel to second wall 420. Third wall 430 is parallel to fourth wall 440. Test section 400 contains room for test subject 401 and various testing equipment (not pictured) that a user may perform desired tests upon. A user can measure the properties of the wave or its effect on an object in test section 400.

FIG. 8 shows end-wave eliminator 500. End-wave eliminator 500 contains shock diffuser 510 within enclosing dump tank 520. In some embodiments, shock diffuser 510 has a converging cross-sectional area with porous surface 511. For example, shapes with converging cross-sectional areas include wedges, cones, or pyramids. In some embodiments, the converging cross-sectional area of shock diffuser 510 matches that of test section 200. When a shockwave enters end-wave eliminator 500, it passes through shock diffuser 510, and is propelled through porous surface 511 (shown here with cross-sectional shading) into enclosing dump tank 520, where enclosing dump tank 520 has sufficient volume to hold the volume of gas in the waveform and an anechoic lining to dissipate the sound of the waveform.

In some embodiments, porous surface 511 may be a perforated plate, a wire mesh, expanded metal, or any other material that provides controlled and distributed venting of the shock wave flow from test section 400. A wire mesh cone that is a spiral wrapped with strong non-adhesive tape will also serve this purpose. In this embodiment, the spiral wrapping allows controlled venting between the leaves of the overlapping tape laps. The porous feature of porous surface 511 must be adjusted so that the net effect is to cause elimination of any appreciable upstream reflection while allowing for the controlled efflux of the shock wave gas from test section 400 into dump tank 520. In this embodiment, the end-wave eliminator dissipates the energy in the waveform leaving the test section.

A blast wave is a single-pulse event, but standard shock tubes develop longitudinal reverberant wave patterns due to the ultimate reflection of the shock wave at the end of the tube. If the tube has a closed end, that closed end will cause a reflected shock of greatly enhanced pressure, to be propagated back toward to the test area stopping the outflow. Conversely, an open end will cause a rarefaction wave of reduced pressure, enhancing outflow back to the test area. These anomalous pressure waves are known as "end waves."

One solution to the problem of end waves, in facilities without space limitations, is to have a sufficiently long shock tube from the experiment section to the end of the shock tube, such that the arrival of a reflective disturbance from the end of the shock tube does not affect the experiment in the time scale of interest. However, this creates two problems. First, many facilities have space limitations that cannot handle a shock tube of a sufficient length to make reflection irrelevant to the experiment. Second, some targets, such as biological material specimens, are affected by all waves during that target's time in the shock tube. These anomalous waves will cause the experiment to produce inaccurate results.

While reflection eliminators have been designed for shock tubes in the past, embodiments of the present invention utilize dump tank 520, in combination with shock diffuser 510, to eliminate anomalous waves in the most complete manner possible. Additionally, end-wave eliminator 500 also mitigates potentially hazardous and disturbing noise, and flow efflux, into the surrounding laboratory space.

That which is claimed:

1. A blast wave simulator comprising:
   a driver section containing an apex having a first end wherein the first end continuously opens and expands to a second end which is distal upon the shock tube driver such that a cross sectional area of the shock tube driver between the first end and the second end is constantly changing;
   a frangible membrane proximate the second end;
      wherein the apex contains equipment to pressurize the shock tube driver, which causes the frangible membrane to rupture; and which creates the blast pressure wave having a primary shock phase and a secondary shock phase;
   wherein the secondary shock phase further comprises a secondary phase of compression
   a transition section mechanically coupled to the driver section;
      which is capable of manipulating the pressure wave and has a physical geometry which diverges from that of the driver section;
   a test section mechanically coupled to the transition section;
      where the test section contains a testing equipment to measure an effect of the pressure wave on a test subject; and
   an end-wave eliminator mechanically coupled to the test section;
      where the end-wave eliminator dissipates the pressure wave.

2. The blast wave simulator of claim 1, where the equipment to pressurize the driver section further comprises:
   a flammable gas inlet and a set of firing plugs
      where the set of firing plugs ignite a flammable gas in the driver section
      which pressurizes the driver section and
      which creates the pressure wave in the blast wave simulator upon the rupture of the frangible membrane.

3. The blast wave simulator of claim 1, where the equipment to pressurize the driver section further comprises:
   an air-eductor purge port that enables an air compressor to pressurize the driver section with compressed gas
   where the compressed gas creates the pressure wave once the frangible membrane ruptures.

4. The blast wave simulator of claim 1 where the equipment to pressurize the driver section the driver section further comprises:
   a balloon in the apex that is inflated by an inflation means;
   where the balloon is the frangible membrane;
   where over-pressurization of the balloon causes the balloon to rupture
   which pressures the driver section and
   which creates the pressure wave.

5. The blast wave simulator of claim 1 where the transition section further comprises:
   a support strut where the support strut both provides support for the frangible membrane and
   the support strut contains a mechanism for cutting the frangible membrane.

6. The blast wave simulator of claim 1 where the transition section further comprises:
   the physical geometry that can be represented by a function which has a first derivative that is continuous throughout a length of the transition section, and
   the physical geometry that can be represented by the function which has a second derivative that is continuous throughout the length of the transition section and is of a low order.

7. The blast wave simulator of claim 1, where the transition section further comprises:
   louvered apertures in a set of side walls of the transition section that allow for pressure to escape from the blast wave simulator.

8. The blast wave simulator of claim 1, where the end-wave eliminator further comprises:
   a shock diffuser that displaces the pressure wave leaving the test section, and
   a dump tank with a sufficient volume to contain a volume of gas created by the driver section.

9. A shock tube driver configured to form a blast pressure wave, comprising:
   an apex having a first end wherein the first end continuously opens and expands to a second end which is distal upon the shock tube driver such that a cross sectional area of the shock tube driver between the first end and the second end is constantly changing;
   a frangible membrane proximate the second end;
   wherein the apex contains equipment to pressurize the shock tube driver, which causes the frangible membrane to rupture; and which creates the blast pressure wave having a primary shock phase and a secondary shock phase; wherein the secondary shock phase further comprises a secondary phase of compression.

10. The shock tube driver of claim 9, wherein the primary shock phase further comprises a first impulse having a pressure that is initially high, then a first phase of compression below atmospheric pressure and wherein the secondary shock phase further comprises a second impulse, followed by the second phase of compression.

11. The shock tube driver of claim 9, further comprising:
a physical geometry that enables the blast pressure wave to have a primary shock phase and a secondary shock phase;
wherein the physical geometry has a first part with a positive curvature and a second part with a negative curvature;
wherein the second part is mechanically coupled to a cutting mechanism configured to cut the frangible membrane without disrupting the blast pressure wave.

12. The shock tube driver of claim 9, further comprising:
a physical geometry enabling the pressure wave to have a primary shock phase and a secondary shock phase
where the physical geometry has a first part with a linear curvature and a second part with an convergent curvature.

13. The shock tube driver of claim 9, further comprising:
a physical geometry enabling the pressure wave to have a primary shock phase and a secondary shock phase
where the physical geometry has a first part with a negative curvature and a second part with a convergent curvature.

14. The shock tube driver of claim 9, further comprising:
a physical geometry enables the pressure wave to have a primary shock phase and a secondary shock phase;
where the physical geometry includes a plurality of shock tube drivers.

15. The shock tube driver of claim 9, where the equipment to pressurize the shock tube driver further comprises:
a flammable gas inlet and a set of firing plugs;
where the set of firing plugs ignite a flammable gas in the shock tube driver;
which pressurizes the shock tube driver; and
which creates the blast pressure wave.

16. The shock tube driver of claim 9, where the equipment to pressurize the shock tube driver further comprises:
a port used by an air compressor to pressurize the shock tube driver with compressed gas;
where the compressed gas creates the pressure wave once the frangible membrane ruptures.

17. The shock tube driver of claim 9, where the equipment to pressurize the shock tube driver further comprises:
a balloon in the apex that is inflated by an inflation device;
where over-pressurization of the balloon causes the balloon to rupture
which pressurizes the shock tube driver; and
which creates the blast pressure wave upon the rupture of the balloon.

18. The shock tube driver of claim 9 where the equipment to pressurize the shock tube driver further comprises:
a balloon in the apex that is inflated by an inflation device;
where a cutting device causes the balloon to rupture;
which pressurizes the shock tube driver; and
which creates the blast pressure wave upon the rupture of the balloon.

* * * * *